United States Patent [19]

Sekikawa et al.

[11] Patent Number: 4,780,317

[45] Date of Patent: Oct. 25, 1988

[54] SUSTAINED RELEASE ANTIMICROBIAL AGENTS AND METHOD OF FOULING CONTROL USING THE SAME

[75] Inventors: Ayako Sekikawa, Hatano; Hideo Sugi, Yokohama; Kenji Tahara, Atsugi; Fumio Toda, Onsen, all of Japan

[73] Assignee: Kurita Water Industries Ltd., Tokyo, Japan

[21] Appl. No.: 6,050

[22] Filed: Jan. 22, 1987

[30] Foreign Application Priority Data

Jan. 28, 1986 [JP] Japan ................... 61-16033

[51] Int. Cl.$^4$ .................. A61K 9/22; C23F 11/04; C09D 5/16
[52] U.S. Cl. .................. 424/468; 106/15.05; 106/18.33; 422/6; 422/7; 422/14; 422/16; 424/405; 424/406; 424/408; 514/359; 514/439; 514/445; 514/964
[58] Field of Search .............. 424/406, 408; 106/15.05, 18.33; 514/359, 439, 445, 964

[56] References Cited

U.S. PATENT DOCUMENTS 2,514,868  7/1950  Hubbell ................. 424/405
3,801,575  4/1974  Lewis et al. ........... 523/122 X
3,928,198  12/1975  Brink, Jr. et al. ....... 106/18.33 X
4,243,403  1/1981  Lewis et al. ........... 106/18.33 X
4,465,795  8/1984  Sunano et al. ......... 106/15.05 X
4,539,071  9/1985  Clifford et al. ........ 106/18.33 X
4,552,591  11/1985  Millar ................. 106/18.33
4,644,021  2/1987  Toda et al. ........... 523/122
4,661,528  4/1987  Rei .................... 523/122 X Primary Examiner—Thurman K. Page
Attorney, Agent, or Firm—Frank J. Jordan; C. Bruce Hamburg; Manabu Kanesaka

[57] ABSTRACT

A sustained release antimicrobial agent comprises a clathrate compound composed of a water-soluble microbicide and at least one of the compounds shown at (I) to (V) below:

(I) 1,1'-bi-2-naphthol;
(II) 1,1,4,4-tetraphenyl-2-butyn-1,4-diol;
(III) 9,10-di(4-methylphenyl)-9,10-dihydroznthracene-9,10-diol;
(IV) 1,1-bis(4-hydroxyphenyl)-cyclohexane; and
(V) 1,1,6,6-tetra(2,4-dimethylphenyl)-2,4-hexadiyne-1,6-diol.

A method which uses it for preventing the fouling of a water system is also disclosed.

22 Claims, No Drawings

SUSTAINED RELEASE ANTIMICROBIAL AGENTS AND METHOD OF FOULING CONTROL USING THE SAME

FIELD OF THE INVENTION AND RELATED ART STATEMENT

This invention relates to sustained release antimicrobial agents and methods of fouling control using the same. More particularly, it relates to sustained release antimicrobial agents capable of maintaining their antimicrobial activity over long period and to methods of fouling control using the same.

The slime of animal, plant or fungi tends to deposit and causes various problems in cooling water systems of various industrial facilities, the water systems of the paper and pulp industry, etc.

The deposition of the slime of zoogloea, algae or filamentous fungi in the cooling water systems lowers their thermal efficiency, adversely affects their circulation of water and gives rise to the corrosion of their metallic parts.

In the paper and pulp industry, the slime of bacteria, filamentous fungi, yeast, etc. is mainly produced in the paper mill process. If any such slime is carried over into a pulp slurry, it causes a number of problems. It not only results in the lowering of product quality, but also gives rise to the breakage of paper leading to a drastic reduction in production efficiency. The use of recirculated water has recently been increasing in the paper and pulp industry. It makes the control of slime an issue of greater importance.

In thermoelectric power plants, ironworks and other factories using seawater, marine algae and bacteria, mytilus, protochordata and other living things gather at the seawater intakes and on the internal surfaces of cooling pipes and lower their functions. They are carried away by flowing water and clog other parts, such as tubes of heat exchangers and strainers. They retard the flow of water therethrough and eventually lower the performance of the entire system.

In order to prevent such trouble arising from the deposition of slime, microorganisms or shellfishes, it has been customary to use antimicrobial agents (slime control agents) because of their easy application and low cost. Water-soluble antimicrobial agents, such as hydrazine ($N_2H_4$) or isothiazoline compounds, are, among others, in common use. Among these compounds, 5-chloro-2-methyl-4-isothiazolin-3-one (hereinafter referred to simply as "CMI"), which is represented by formula (I) below, has a particularly high degree of antimicrobial activity and is widely used as a slime controller, bactericide, algicide or fungicide in cooling water systems, water systems in the paper and pulp industry, swimming pools and other water systems:

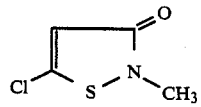
(I)

CMI is usually produced by:
(1) the halogenation of β-thioketoamide in an inert organic ester solvent, such as acetic acid ester, or
(2) the treatment of a β-substituted thiocyanoacrylamide or thiosulfatoacrylamide with an acid to obtain isothiazolone and the halogenation thereof, as disclosed in Japanese Patent Publication No. 21240/1971. KA-THON 886 is the tradename of CMI sold by Rohm & Haas.

Both of these two methods (1) and (2), however, fail to give a product which is composed solely of CMI. It contains 2-methyl-4-isothiazolin-3-one (hereinafter referred to simply as "MI"), which is represented by formula (II) below and of which the antimicrobial activity is as low as only one-tenth of that of CMI:

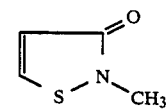
(II)

Moreover, there is not known any method that makes it possible to isolate CMI from the reaction product.

Although CMI is a substance having a high degree of antimicrobial activity, its handling requires a great deal of care, as it is highly irritant to the skin. When it is used in water, it is difficult to maintain its antimicrobial activity for a long period of time, as it reacts with organic substances in water, such as amines and reducing substances, and thereby loses its activity. No antifouling paint containing CMI can maintain its antifouling effect for a long period of time when it is used in water, as CMI is easily soluble in water.

The water-soluble antimicrobial agents which have hitherto been commonly used are far from satisfactory, since they are toxic and require a great deal of care when they are handled, lower their antimicrobial activity rapidly and are highly soluble in water.

OBJECT AND SUMMARY OF THE INVENTION

It is an object of this invention to overcome the drawbacks of the prior art as hereinabove pointed out and provide a sustained release antimicrobial agent having a high degree of antimicrobial activity and a method for fouling control using the same.

It is another object of this invention to provide a sustained release antimicrobial agent which can maintain its antimicrobial activity for a very long period of time and a method for fouling control using it.

It is a further object of this invention to provide a sustained release antimicrobial agent which is low in toxicity and easy to handle, and a method for fouling control using it.

These objects are attained by a sustained release antimicrobial agent comprising a clathrate compound composed of a water-soluble microbicide and at least one compound selected from the group of compounds represented by the following formulas (I) to (V):

(I) 1,1'-bi-2-naphthol (which will sometimes be referred to simply as "β-dinaphthol")

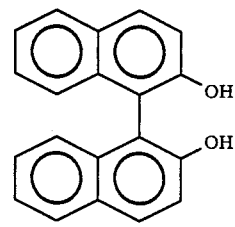

(II) 1,1,4,4-tetraphenyl-2-butyn-1,4-diol (which will sometimes be referred to simply as "TPB")

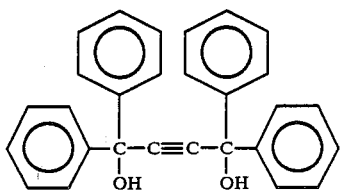

(III) 9,10-di(4-methylphenyl)-9,10-dihydroanthracene-9,10-diol (which will sometimes be referred to simply as "PhHA")

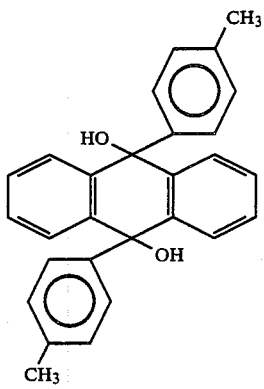

(IV) 1,1-bis(4-hydroxyphenyl)-cyclohexane (which will sometimes be referred to simply as "PhCH")

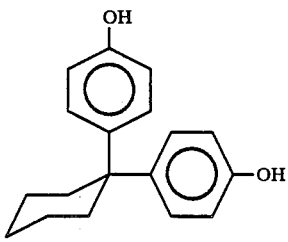

(V) 1,1,6,6-tetra(2,4-dimethylphenyl)-2,4-hexadiyne-1,6-diol (which will sometimes be referred to simply as "TDPh")

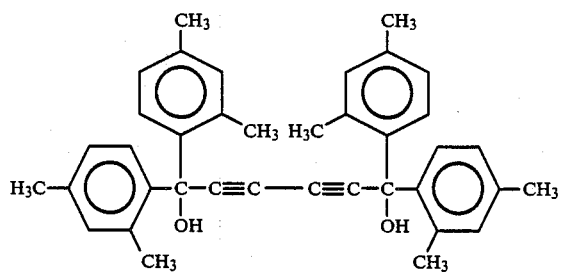

and by a method for fouling control which comprises treatment with a clathrate compound composed of a water-soluble microbicide and at least one compound selected from the group of compounds represented by the formulas (I) to (V).

DETAILED DESCRIPTION OF PREFERRED EMBODIMENTS

The invention will now be described in further detail.

According to this invention, it is possible to use any water-soluble microbicide that can form a clathrate compound with β-dinaphthol, TPB, PhHA, PhCH or TDPh. Hydrazine and CMI, which are widely used as an effective microbicide, are typical examples, but it is also possible to use other compounds, such as bromonitroalcohol, dithiol-3-one, 2,2-dibromo-3-nitropropionamide, thiocyanate or their derivatives.

The clathrate compound which is composed of a water-soluble microbicide and any of the compounds according to formulas (I) to (V) can be prepared from the following materials (a) to (c):

(a) A solution of any of the compounds according to formulas (I) to (V) in a solvent selected from methanol, ethanol, n-propanol, acetone, benzene, chloroform, an ester such as ethyl acetate, an ether such as dipropyl ether, etc.;

(b) A water-soluble microbicide, such as CMI or hydrazine; and (c) A mixture of a water-soluble microbicide and impurities.

The material (b) or (c) is gradually added to (a) so that they may react with each other. The reaction product is left to stand for some time, or the solvent is removed by vaporization if required, whereby a dark black precipitate is obtained if a compound of formula (I) has been used, or a slightly opaque precipitate if a compound of any of formulas (II) to (V) has been used. The precipitate is separated by a customary method, as by . using filter paper, to yield the intended clathrate compound.

This method has a great advantage, since it can prepare a clathrate compound composed of only the effective components, even if the starting microbicide may be a mixture containing any byproduct or other impurities.

The solvent to be used for preparing the solution (a), the method of preparing the clathrate compound and the form of the precipitate which can be obtained depend to some extent or other upon the compound of any of formulas (I) to (V) which is used for forming the clathrate compound with the microbicide.

If the compound of formula (I) (β-dinaphthol) is used, it is preferable to use a solvent such as methanol or ethanol. The reaction product is a dark black precipitate.

If the compound of formula (II) (TPB) is used, it is preferable to use a solvent such as benzene, chloroform, ethyl acetate or dipropyl ether. If the solvent is removed by vaporization from the reaction product, there is obtained a colorless and transparent crystalline precipitate.

If the compound of formula (III) (PhHA) is used, it is preferable to use a solvent such as chloroform, benzene, ester or ether. If the reaction product is left to stand overnight, there is obtained a white planar precipitate.

If the compound of formula (IV) (PhCH) is used, it is preferable to use a solvent such as benzene, acetone or n-butyl ether. The reaction product is a colorless and transparent crystalline precipitate or a green and opaque precipitate.

If the compound of formula (V) (TDPh) is used, it is preferable to use a solvent such as methanol, ethanol or n-propanol. The reaction product is a slightly opaque precipitate.

The clathrate compound is formed by the inclusion of the guest molecules or the molecules of the water-soluble microbicide such as CMI, in the host molecules or the molecules of the molecules compound according to any of formulas (I) to (V). It is obtained as a result of any of the following reactions, though there may occur some differences from the conditions under which it is prepared:

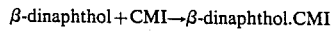
β-dinaphthol+CMI→β-dinaphthol.CMI

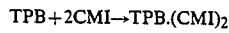
TPB+2CMI→TPB.(CMI)$_2$

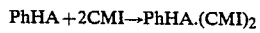
PhHA+2CMI→PhHA.(CMI)$_2$

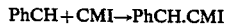
PhCH+CMI→PhCH.CMI

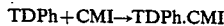
TDPh+CMI→TDPh.CMI

The sustained release antimicrobial agent of this invention may comprise a single clathrate compound composed of a water-soluble microbicide and one of the compounds of formula (I) to (V), or two or more clathrate compounds formed by employing two or more compounds of formulas (I) to (V), respectively.

Any clathrate compound obtained as hereinabove described is usually a powdery solid and is, therefore, easy to form into tablets or any other shape. It is low in toxicity and is, therefore, easy to handle, since the molecules of the microbicide are included in the host molecules.

The sustained release antimicrobial agent of this invention may contain a binder, a solvent, a carrier, a humectant, a filler or any other component, as required, in addition to the clathrate compound. The agent of this invention contains preferably at least 1%, more preferably 1 to 100%, and still more preferably, 5 to 50%, by weight of the clathrate compound.

The slime control method of this invention comprises treating water in a water system or the surfaces of equipment in the system with the sustained release antimicrobial agent of this invention containing the clathrate compound. The method is carried out in any of the following ways:

(1) The water to be treated is allowed to flow through a column packed with the agent;
(2) Bags or cartridges of a material which is permeable to water, but not soluble therein, are filled with the agent and are submerged or floated in the water to be treated;
(3) The powdery agent or any shaped product thereof is dispersed in the water to be treated;
(4) A mixture of the agent with a paint or any other resinous coating material is applied to the surfaces of equipment in the water system to be protected;
(5) The agent is bonded by an appropriate method, as using an adhesive, to the surfaces to be protected; and
(6) Molded product in a form such as a sheet which is produced by polymerizing or curing the agent and synthetic resin after mixing thereof is immersed into the water system to be treated.

As is obvious from the foregoing, the sustained release antimicrobial agent of this invention comprises a clathrate compound which contains as its effective component a water-soluble microbicide included in any of the compounds according to formulas (I) to (V). Therefore, it has, among others, the following advantages:

(1) It can maintain its antimicrobial activity for a very long period of time, since its effective component is only gradually dissolved in the water to be treated;
(2) As it is a solid, it can be formed into tablets or any other shape that facilitates its handling;
(3) It has an improved degree of safety and provides an improved working environment, since the clathrate compound lowers the toxicity of the water-soluble microbicide and its irritation to the skin; and
(4) Its effective component does not react with any other substance and lower its antimicrobial activity.

The fouling control method of this invention, which comprises treatment with any such highly effective clathrate compound, can effectively and easily prevent the deposition of any slime, microorganism or shellfish and thereby ensure the elimination of any trouble that has hitherto been caused by such deposition.

The invention will now be described more specifically by way of example. It is, however, to be understood that the following description is not intended to limit the scope of this invention, but that variations or modifications may be easily made by anybody of ordinary skill in the art without departing from the scope of this invention which is defined by the appended claims.

EXAMPLE 1

Preparation of Clathrate Compounds

Preparation of β-dinaphthol.CMI:

To a β-dinaphthol solution obtained by dissolving 5.05 g ($1.74\times10^{-2}$ mole) of β-dinaphthol in 100 ml of methanol were added 30.8 g of a solution containing CMI and MI in a weight ratio of 3.4:1, which amount contained 2.36 g ($1.75\times10^{-2}$ mole) of CMI. The mixed solution was stirred to yield a reaction product containing a dark black precipitate. It was allowed to stand at room temperature for 16 hours. Then, the precipitate was separated from the solution by filtration and collected on filter paper.

The NMR analysis of the precipitate revealed that it contained β-dinaphthol and CMI in a molar weight ratio of 1:1 and in a weight ratio of 65.7:34.3. Its elemental analysis confirmed that it did not contain any MI.

Preparation of TPB.(CMI)$_2$:

One gram ($5.12\times10^{-3}$ mole) of the solution containing CMI and MI in a ratio of 3.4:1 was added to a TPB solution obtained by dissolving 1 g ($2.56\times10^{-3}$ mole) of TPB in 100 ml of benzene. After the mixed solution had been stirred, it was allowed to stand at room temperature for 10 days for the vaporization of the benzene to yield a colorless and transparent crystalline precipitate. The precipitate was separated from the solution by filtration and collected on filter paper.

The NMR analysis of the precipitate revealed that it contained TPB and CMI in a molar ratio of 1:2 and in a weight ratio of 56.6:43.4. It did not contain any MI.

Preparation of PhHA.(CMI)$_2$:

To a PhHA solution obtained by dissolving 2 g ($5.10\times10^{-3}$ mole) of PhHA in 50 ml of chloroform were added 1.95 g ($10.1\times10^{-3}$ mole) of the solution containing CMI and MI in a weight ratio of 3.4:1. The mixed solution was stirred and allowed to stand, whereby a white planar crystalline precipitate was obtained. The precipitate was separated from the solution by filtration and collected on filter paper.

The NMR analysis of the precipitate revealed that it contained PhHA and CMI in a molar ratio of 1:2 and in a weight ratio of 56.7:43.3. It did not contain any MI.

Preparation of PhCH.CMI:

Added to a PhCH solution obtained by dissolving 2 g ($7.45 \times 10^{-3}$ mole) of PhCH in 80 ml of benzene were 2.86 g ($14.9 \times 19^{-3}$ mole) of the solution containing CMI and MI in a weight ratio of 3.4:1. After the mixed solution had been stirred, it was allowed to stand at room temperature overnight, whereby a colorless and transparent flaky crystal was precipitated on the interface between benzene and water.

The precipitate was picked up with a pincette and the reaction solution was allowed to stand overnight again. As a result, a colorless and transparent flaky crystal was precipitated again on the interface. It was also picked up with the pincette.

The NMR analysis of each precipitate revealed that it contained PhCH and CMI in a molar ratio of 1:1 and in a weight ratio of 64.2:35.8. It did not contain any MI.

Preparation of TDPh.CMI:

Added to a TDPh solution obtained by dissolving 2 g ($3.80 \times 10^{-3}$ mole) of TDPh in 40 ml of n-propanol were 7.3 g ($38 \times 10^{-3}$ mole) of the solution containing CMI and MI in a weight ratio of 3.4:1. After the mixed solution had been stirred, it was allowed to stand, whereby a turbid precipitate was obtained. It was separated from the solution by filtration and collected on filter paper.

The NMR analysis of the precipitate revealed that it contained TDPh and CMI in a molar ratio of 1:1 and in a weight ratio of 77.9:22.1. It did not contain any MI.

CMI Dissolution Test:

Each of the clathrate compounds which had been obtained was placed in a 0.8 μ membrane filter bag in an amount containing 0.1 g of CMI, while 0.1 g of CMI was also placed in another bag. Each bag was immersed in one liter of pure water. While the water was being stirred by a stirrer, the concentration of CMI in the water was measured at certain intervals so that the change of its concentration with the lapse of time might be acertained. The results are shown in Table 1.

TABLE 1

Unit: ppm

| Time elapsed | 10 min. | 30 min. | 1 hour | 2 hours | 4 hours |
|---|---|---|---|---|---|
| CMI alone | 100 | 100 | 100 | 100 | 100 |
| β-dinaphthol · CMI | 12 | 33 | 69 | 90 | — |
| TPB · (CMI)$_2$ | 15 | 40 | 75 | 96 | 100 |
| PhHA · (CMI)$_2$ | 13 | 33 | 67 | 92 | 100 |
| PhCH · CMI | 14 | 38 | 70 | 92 | 100 |
| TDPh · CMI | — | — | — | — | — |

| Time elapsed | 8 hours | 1 day | 2 days | 4 days | 6 days |
|---|---|---|---|---|---|
| CMI alone | 100 | 100 | 100 | 100 | 100 |
| β-dinaphthol · CMI | 100 | — | — | — | — |
| TPB · (CMI)$_2$ | 100 | — | — | — | — |
| PhHA · (CMI)$_2$ | 100 | — | — | — | — |
| PhCH · CMI | 100 | — | — | — | — |
| TDPh · CMI | — | 8 | 24.2 | 17.5 | 22.2 |

As is obvious from Table I, CMI was gradually released from any of the clathrate compounds according to this invention, but when used alone, it was dissolved immediately after the filter bag had been immersed in water. It is, therefore, obvious that the antimicrobial agent of this invention comprising any such clathrate compound can sustain the release of its effective component and maintain its antimicrobial activity for a long period of time.

What is claimed is:

1. A sustained release antimicrobial agent comprising a clathrate compound of a water-soluble microbicide and at least one compound selected from the group consisting of the compounds shown at (I) to (V) below:

1,1'-bi-2-naphthol      (I)

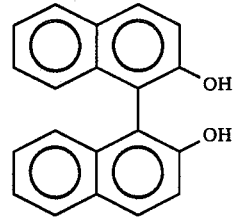

1,1,4,4-tetraphenyl-2-butyn-1,4-diol      (II)

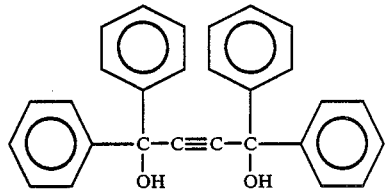

9,10-di(4-methylphenyl)-9,10-dihydroanthracene-9,10-diol      (III)

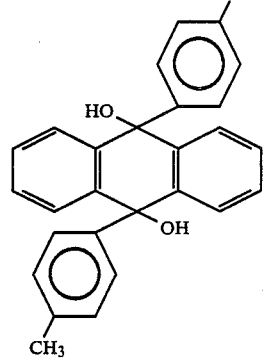

1,1-bis(4-hydroxyphenyl)-cyclohexane      (IV)

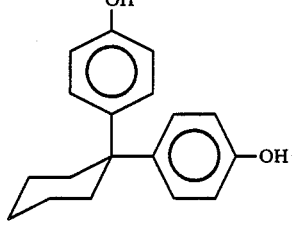

1,1,6,6-tetra(2,4-dimethylphenyl)-2,4-hexadiyne-1,6-diol      (V)

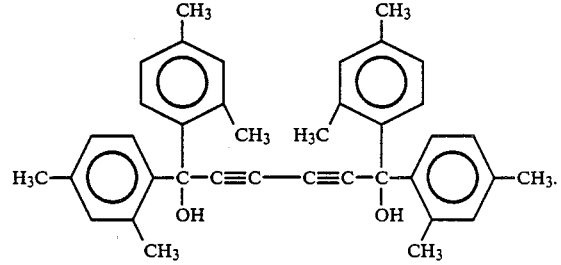

2. A sustained release antimicrobial agent as set forth in claim 1, wherein said water-soluble microbicide is 5-chloro-2-methyl-4-isothiazolin-3-one.

3. A sustained release antimicrobial agent as set forth in claim 1, wherein said water-soluble microbicide is hydrazine.

4. A sustained release antimicrobial agent as set forth in claim 1, wherein said clathrate compound is contained in the amount of 1 to 100% by weight.

5. A sustained release antimicrobial agent as set forth in claim 1, wherein said clathrate compound is contained in the amount of 5 to 50% by weight.

6. A sustained release antimicrobial agent as set forth in claim 1, wherein said clathrate compound is in the form of tablets.

7. A method of preventing the fouling of a water system which comprises treatment with a clathrate compound composed of a water-soluble microbicide and at least one compound selected from the group consisting of the compounds shown at (I) to (V) below:

1,1'-bi-2-naphthol (I)

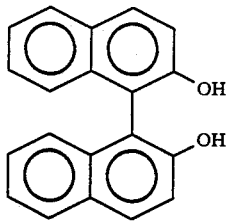

1,1,4,4-tetraphenyl-2-butyn-1,4-diol (II)

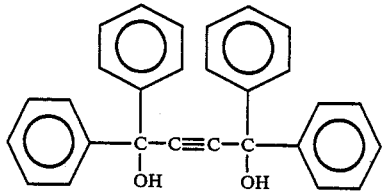

9,10-di(4-methylphenyl)-9,10-dihydroanthracene-9,10-diol (III)

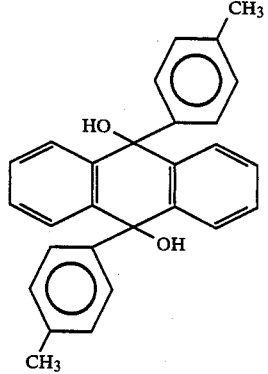

1,1-bis(4-hydroxyphenyl)-cyclohexane (IV)

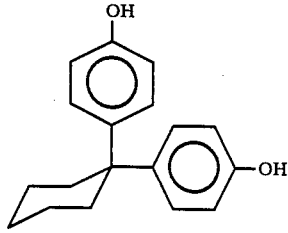

1,1,6,6-tetra(2,4-dimethylphenyl)-2,4-hexadiyne-1,6-diol (V)

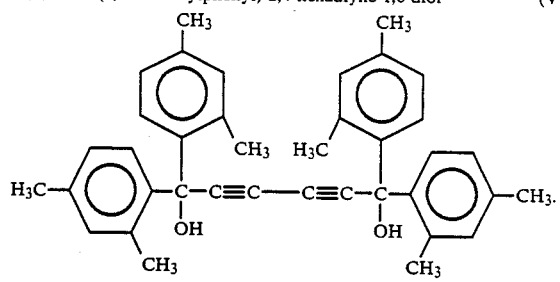

8. A method as set forth in claim 7, wherein said treatment is carried out by allowing water in said water system to flow through a column packed with said clathrate compound.

9. A method as set forth in claim 7, wherein said treatment is carried out by submerging or floating in said water system a container holding said clathrate compound, said container being formed from a material which is permeable to water, but not soluble therein.

10. A method as set forth in claim 7, wherein said treatment is carried out by dispersing said clathrate compound in said water system, said clathrate compound being powdery o appropriately shaped.

11. A method as set forth in claim 7, wherein said treatment is carried out by causing said clathrate compound to adhere to the surface of any equipment in said water system, said clathrate compound being powdery or appropriately shaped.

12. A method as set forth in claim 7, wherein said treatment is carried out by coating the surface of any equipment in said water system with a mixture of said clathrate compound and a resin.

13. A sustained release antimicrobial agent as set forth in claim 1, wherein the compound for forming a clathrate compound together with water-soluble microbicide is:

1,1'-bi-2-naphthol

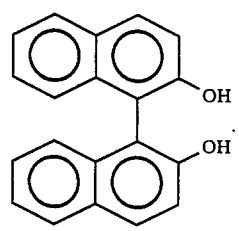

14. A sustained release antimicrobial agent as set forth in claim 1, wherein the compound for forming a clathrate compound together with water-soluble microbicide is:

1,1,4,4-tetraphenyl-2-butyn-1,4-diol

-continued

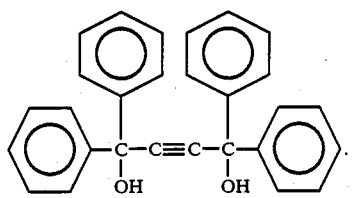

15. A sustained release antimicrobial agent as set forth in claim 1, wherein the compound for forming a clathrate compound together with water-soluble microbicide is:

9,10-di(4-methylphenyl)-9,10-dihydroanthracene-9,10-diol

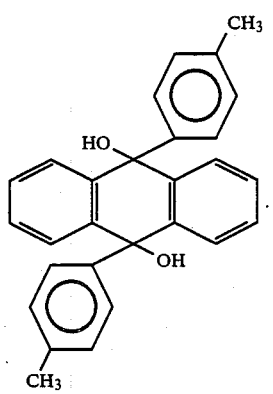

16. A sustained release antimicrobial agent as set forth in claim 1, wherein the compound for forming a clathrate compound together with water-soluble microbicide is:

1,1-bis(4-hydroxyphenyl)-cyclohexane

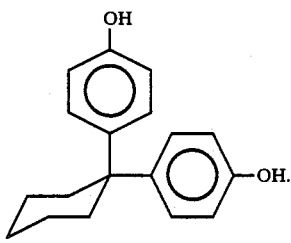

17. A sustained release antimicrobial agent as set forth in claim 1, wherein the compound for forming a clathrate compound together with water-soluble microbicide is:

1,1,6,6-tetra(2,4-dimethylphenyl)-2,4-hexadiyne-1,6-diol

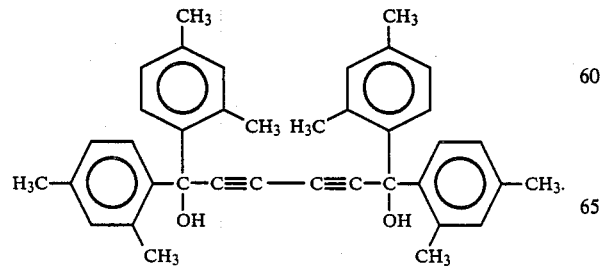

18. A method as set forth in claim 7, wherein the compound for forming a clathrate compound together with water-soluble microbicide is:

1,1′-bi-2-naphthol

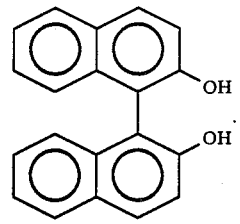

19. A method as set forth in claim 7, wherein the compound for forming a clathrate compound together with water-soluble microbicide is:

1,1,4,4-tetraphenyl-2-butyn-1,4-diol

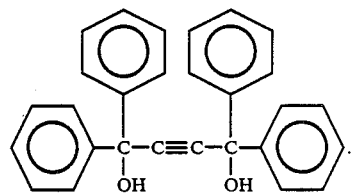

20. A method as set forth in claim 7, wherein the compound for forming a clathrate compound together with water-soluble microbicide is:

9,10-di(4-methylphenyl)-9,10-dihydroanthracene-9,10-diol

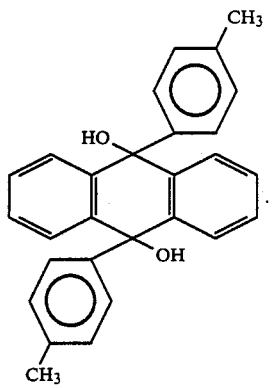

21. A method as set forth in claim 7, wherein the compound for forming a clathrate compound together with water-soluble microbicide is:

1,1-bis(4-hydroxyphenyl)-cyclohexane

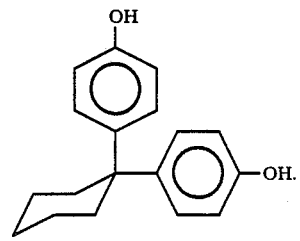

22. A method as set forth in claim 7, wherein the compound for forming a clathrate compound together with water-soluble microbicide is:
1,1,6,6-tetra(2,4-dimethylphenyl)-2,4-hexadiyne-1,6-diol
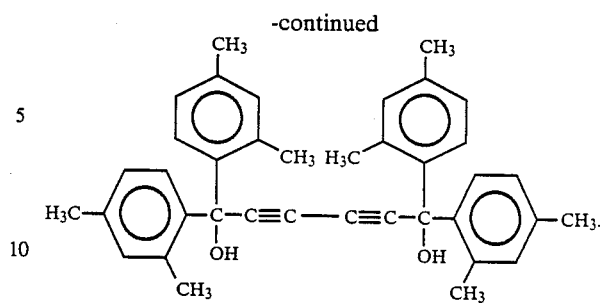
* * * * *